US006057331A

United States Patent [19]

Duvert

[11] Patent Number: 6,057,331

[45] Date of Patent: May 2, 2000

[54] SYNERGISTIC FUNGICIDAL COMPOSITION COMPRISING A COMPOUND ANALOGOUS TO STROBILURIN

[75] Inventor: Patrice Duvert, Lyons, France

[73] Assignee: Rhone-Poulenc Agrochimie, Lyons, France

[21] Appl. No.: 09/051,199

[22] PCT Filed: Oct. 2, 1996

[86] PCT No.: PCT/FR96/01532

§ 371 Date: Jul. 2, 1998

§ 102(e) Date: Jul. 2, 1998

[87] PCT Pub. No.: WO97/12520

PCT Pub. Date: Apr. 10, 1997

[30] Foreign Application Priority Data

Oct. 5, 1995 [FR] France .................................. 95 11951

[51] Int. Cl.[7] ............................ A01N 43/50; A01N 43/54

[52] U.S. Cl. ............................................ 514/269; 514/391

[58] Field of Search ..................................... 514/269, 391

[56] References Cited

U.S. PATENT DOCUMENTS

| | | | |
|---|---|---|---|
| Re. 33,989 | 7/1992 | Wenderoth et al. | 514/522 |
| 4,829,085 | 5/1989 | Wenderoth et al. | 514/522 |

FOREIGN PATENT DOCUMENTS

| | | |
|---|---|---|
| 0253213 | 1/1988 | European Pat. Off. . |
| 0398692 | 11/1990 | European Pat. Off. . |
| 0741970 | 11/1996 | European Pat. Off. . |
| 92/08703 | 5/1992 | WIPO . |
| 95/15083 | 6/1995 | WIPO . |

OTHER PUBLICATIONS

Research Disclosure, vol. 338, No. 33893, pp. 506–510 (1992).

Research Disclosure, vol. 348, No. 34874, pp. 267–268 (1993).

Tammes, *Neth. J. Plant Path.,* 70, pp. 73–80 (1964).

Limpel et al, *Proc. NEWCC,* 16, pp. 48–53 (1962).

*The Pesticide Manual,* ed. Clive Tomlin, The British Crop Protection Council, 10$^{th}$ edition, pp. 68, 579, 603–604, 834–835, 1041–1042 (1994).

*Primary Examiner*—Allen J. Robinson
*Attorney, Agent, or Firm*—Burns, Doane, Swecker & Mathis, L.L.P.

[57] ABSTRACT

A synergistic fungicidal composition comprising a compound A having the formula (I)

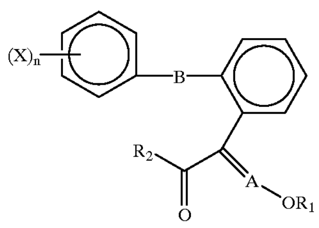

and a compound B which is a dicarboximide derivative such as iprodione, procymidone or vinchlozolin, and a method for controlling or preventing the development of phytopathogenic fungi employing said composition.

22 Claims, 1 Drawing Sheet

SYNERGISTIC FUNGICIDAL COMPOSITION COMPRISING A COMPOUND ANALOGOUS TO STROBILURIN

This application is a 371 of PCT/FR96/01532, filed Oct. 2, 1996.

The subject of the present invention is a synergistic fungicidal composition comprising a compound analogous to strobilurin and a process which makes use of the said composition and which is intended for the curative or preventive protection of crops against fungal attacks.

Compounds analogous to strobilurin with a fungicidal effect are known, in particular from European Patent Application EP 253213 or 398692 or from International Application WO 9208703, which make it possible to prevent the growth and the development of phytopathogenic fungi capable of attacking crops.

However, it is always desirable to improve the spectrum of activity and the effectiveness of such compounds with a fungicidal effect or to reinforce them by combining them with other molecules in order to obtain a more effective product or alternatively to prevent the appearance of fungal strains which are resistant to these new fungicides.

It is also highly desirable to have available fungicidal products which enjoy an improved persistence of effect, likely to space out in time the number of plant-protection treatments necessary for satisfactory control of the parasites.

It is, in any event, particularly advantageous to be able to decrease the amount of chemicals distributed in the environment, while ensuring high-performance protection of crops against fungal attacks.

It has now been found that one (or a number) of the above objectives could be achieved by virtue of the fungicidal composition according to the present invention.

The subject of the present invention is therefore a synergistic fungicidal composition comprising at least one compound A of formula (I):

(I)

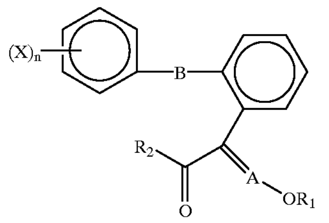

in which:

A is the nitrogen atom or the —CH group,

B is the $—OCH_2—$, $—CH_2—$, $—CH(CH_3)—O—N{=}CH—$ or $—CH{=}N—O—CH(CH_3)—$ group or the group of formula (II):

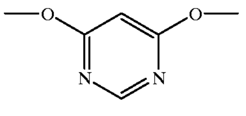

$R_1$ is an alkyl group containing 1 to 4 carbon atoms, preferably the methyl group, $R_2$ is $—OCH_3$ or $—NHCH_3$, X is a halogen atom, the cyano group or an alkyl or haloalkyl group containing 1 to 4 carbon atoms, preferably the methyl or trifluoromethyl group, n is equal to 1 or 2, with, when n is equal to 2, the possibility of having different X groups, and at least one fungicidal compound B chosen from the group comprising dicarboximide derivatives, such as iprodione, procymidone and vinchlozolin, the said composition comprising the components A and B in an A/B ratio by weight of between 0.02 and 5, preferably between 0.0625 and 1.33, with the proviso that when compound B is procymidone, then B in formula (I) is the group of formula (II).

BRIEF DESCRIPTION OF THE DRAWING

The sole FIGURE of Drawing.

Figure 1:
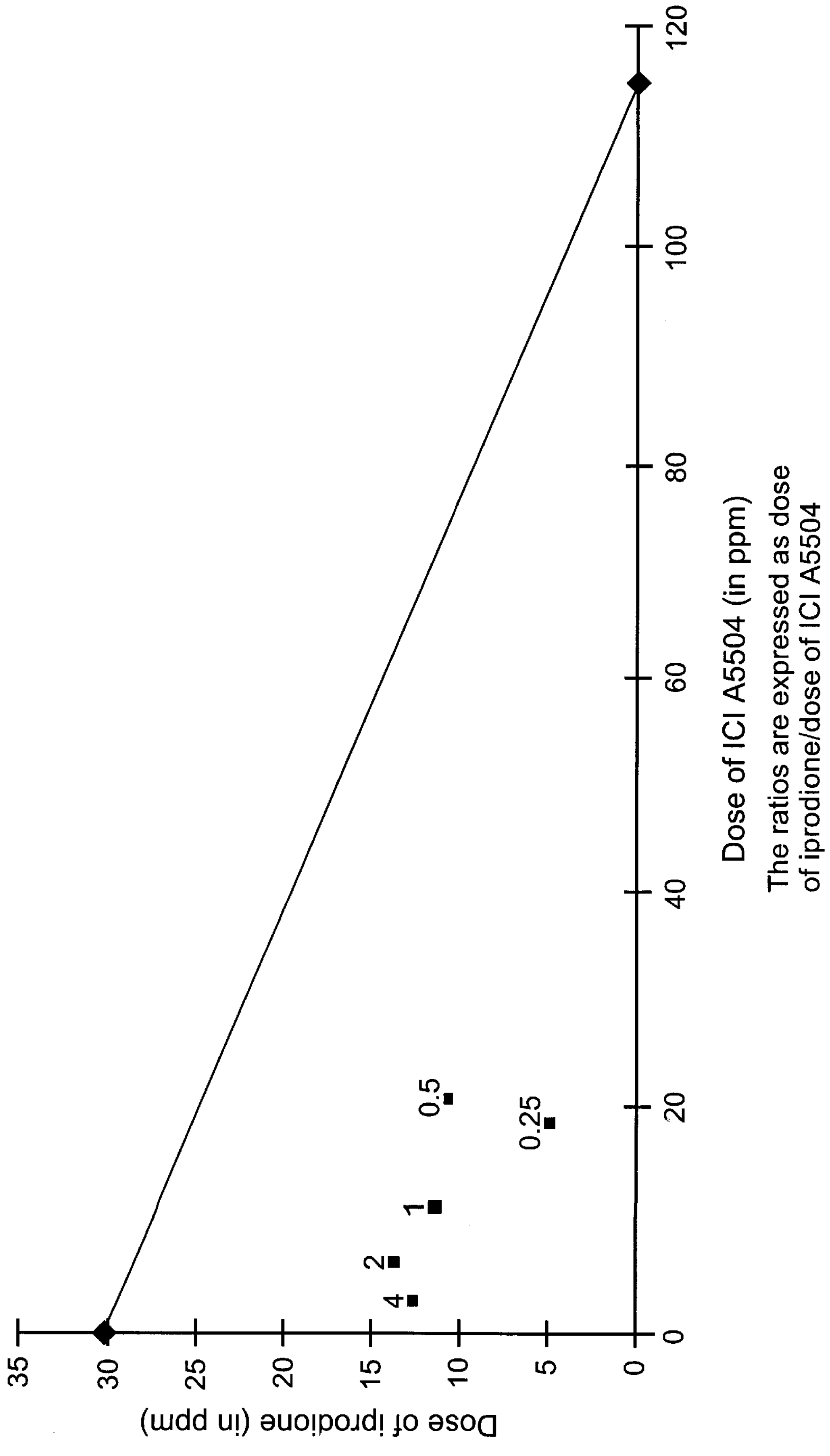
FIG. 1, is an isobole plot for ICIA 5504, i.e. methyl (E)-2-{2-[6-(2-cyanophenoxy) pyrimidin-4-yloxy]phenyl}-3-methoxyacrylate, and iprodione in radish seedlings against *Alternaria brassicae* (alternaria disease).

It is clearly understood that the said fungicidal composition can contain a single compound B or more than one such compound, for example 1, 2 or 3 compounds B, according to the use for which the combination is intended. Likewise, the composition may comprise more than one compound A.

Preference is given to the fungicidal composition according to the invention in which the compound A is methyl (E)-2-{2-[6-(2-cyanophenoxy)pyrimidin-4-yloxy]phenyl}-3-methoxyacrylate, methyl (E)-methoxyimino[α-(o-tolyloxy)-o-tolyl]acetate or N-methyl-(E)-methoxyimino[2-(2,5-dimethylphenoxymethyl)phenyl]acetamide.

Preference is further given, among the more especially preferred meanings of the compound B defined above, to iprodione. In an entirely unexpected way, the composition according to the invention significantly improves the effect of the active materials taken separately with respect to a certain number of fungi which are particularly harmful to crops, for example in particular grapes or the Solanaceae. This improvement is reflected in particular by a decrease in the doses of each of the constituents, which is particularly advantageous for the user and the environment. The fungicidal product thus exhibits synergistic properties attested by application of the Tammes method, "Isoboles, a graphic representation of synergism in pesticides", Netherlands Journal of Plant Pathology, 70(1964), p. 73–80 or as defined by Limpel, L. E., P. H. Schuldt and D. Lammont, 1962, Proc. NEWCC 16:48–53, using the following formula, also called Colby's formula:

$$E=X+Y-X.Y/100$$

in which:

E is the expected percentage inhibition of the growth of the fungus by a mixture of the two fungicides A and B at defined doses, equal to a and b respectively;

X is the observed percentage inhibition by the fungicide A at dose a,

Y is the observed percentage inhibition by the fungicide B at dose b.

When the percentage inhibition observed for the mixture is greater than E, there is synergism.

Preferably, when the component B is iprodione, the A/B ratio is between 0.05 and 5, preferably between 0.17 and 1.33, for all the crops envisaged.

In the particular case of lawns, the A/B ratio will generally be between 0.02 and 2, preferably between 0.0625 and 0.25.

The structures corresponding to the common names of the fungicidal active materials which appear in the definition of B are shown in at least one of the following 2 works:

"The Pesticide Manual", edited by Clive Tomlin and published by The British Crop Protection Council, 10th edition;

l'Index phytosanitaire [Plant-protection index] 1994, published by l'Association de Coordination Technique Agricole [Agricultural Technical Coordination Association], 30th edition.

As regards the derivatives analogous to strobilurin, methyl (E)-2-{2-[6-(2-cyanophenoxy)pyrimidin-4-yloxy] phenyl}-3-methoxyacrylate (or ICIA5504) is described in International Application WO 9208703; methyl (E)-methoxyimino[α-(o-tolyloxy)-o-tolyl]acetate (or BAS490F) is described in European Patent Application EP 253213; and N-methyl-(E)-methoxyimino[2-(2,5-dimethylphenoxymethyl)phenyl]acetamide (or SSF-129) is described in European Patent Application EP 398692. Moreover, ICIA5504 and BAS49OF are listed in the above-mentioned work "The Pesticide Manual".

The fungicidal composition according to the invention comprises, as active material, at least one compound A and at least one compound B as a mixture with solid or liquid vehicles which are acceptable in agriculture and/or surface-active agents which are also acceptable in agriculture. In particular, the inert and conventional vehicles and the conventional surface-active agents can be used. These compositions cover not only compositions which are ready to be applied to the crop to be treated by means of a suitable device, such as a spray device, but also commercial concentrated compositions which have to be diluted before application to the crop. The combination of at least one compound A with at least one compound B is denoted as active material.

These compositions can also contain any kind of other ingredients such as, for example, protective colloids, adhesives, thickening agents, thixotropic agents, penetrating agents, stabilizing agents, sequestering agents and the like. More generally, the compounds A and B can be combined with all the solid or liquid additives corresponding to the conventional formulating techniques.

Generally, the compositions according to the invention usually contain from 0.05 to 95% (by weight) of active material, one or more solid or liquid vehicles and, optionally, one or more surface-active agents.

In the present account, the term "vehicle" denotes a natural or synthetic, organic or inorganic material with which the active material is combined to facilitate its application on the aerial parts of the plant. This vehicle is thus generally inert and it must be acceptable in agriculture, especially on the treated plant. The vehicle can be solid (clays, natural or synthetic silicates, silica, resins, waxes, solid fertilizers and the like) or liquid (water, alcohols, especially butanol, and the like).

The surface-active agent can be an emulsifying, dispersing or wetting agent of ionic or nonionic type or a mixture of such surface-active agents. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols, (especially alkylphenols or arylphenols), salts of esters of sulphosuccinic acids, taurine derivatives (especially alkyltaurates), phosphoric esters of polyoxyethylenated phenols or alcohols, esters of fatty acids and of polyols, and the derivatives of the above compounds containing sulphate, sulphonate and phosphate functional groups. The presence of at least one surface-active agent is generally indispensable when the active material and/or the inert vehicle is/are not soluble in water and the carrier agent for application is water.

The compositions for agricultural use according to the invention can thus contain the active material within very wide limits, ranging from 0.05% to 95% (by weight). Their surface-active agent content is advantageously of between 5% and 40% by weight. Unless otherwise stated, the percentages given in this description, including the claims, are by weight.

These compositions according to the invention are themselves in fairly diverse, solid or liquid forms.

There may be mentioned, as forms of solid compositions, the powders for dusting (with an active material content which can range up to 100%) and the granules, especially those obtained by extrusion, by compacting, by impregnation of a granulated support, or by granulation from a powder (the active material content in these granules being between 0.5 and 80% for the latter cases), the tablets or effervescent tablets.

The fungicidal composition according to the invention can also be used in the form of powders for dusting; it is also possible to use a composition comprising 50 g of active material and 950 g of talc; it is also possible to use a composition comprising 20 g of active material, 10 g of finely divided silica and 970 g of talc; these constituents are mixed and milled and the mixture is applied by dusting.

There may be mentioned, as forms of liquid compositions or those intended to constitute liquid compositions at the time of application, solutions, in particular water-soluble concentrates, emulsifiable concentrates, emulsions, suspension concentrates, aerosols, wettable powders (or powder to be sprayed), pastes or gels.

The emulsifiable or soluble concentrates most often comprise 10 to 80% of active material, the emulsions or solutions ready for application containing, for their part, 0.001 to 20% of active material.

In addition to the solvent, the emulsifiable concentrate may contain, when necessary, 2 to 20% of appropriate additives such as stabilizing agents, surface-active agents, penetrating agents, corrosion inhibitors, colorants or adhesives mentioned above.

Starting from these concentrates, it is possible to obtain, by diluting with water, emulsions of any desired concentration which are particularly suitable for applying to crops.

By way of example, here is the composition of a few emulsifiable concentrates:

EC EXAMPLE 1

| | |
|---|---|
| active material | 400 g/l |
| alkali metal dodecylbenzene sulphonate | 24 g/l |
| oxyethylated nonylphenol with 10 molecules of ethylene oxide | 16 g/l |
| cyclohexanone | 200 g/l |
| aromatic solvent | qs 1 liter |

According to another emulsifiable concentrate formula, the following are used:

EC EXAMPLE 2

| | |
|---|---|
| active material | 250 g |
| expoxidized vegetable oil | 25 g |

-continued

| | |
|---|---|
| mixture of alkylaryl sulphonate and of ether of polyglycol and fatty alcohols | 100 g |
| dimethylformamide | 50 g |
| xylene | 575 g |

The suspension concentrates, which can also be applied by spraying, are prepared so as to obtain a stable fluid product which does not settle out and they generally contain from 10 to 75% of active material, from 0.5 to 15% of surface-active agents, from 0.1 to 10% of thixotropic agents and from 0 to 10% of suitable additives, such as antifoaming agents, corrosion inhibitors, stabilizing agents, penetrating agents and adhesives and, as vehicle, water or an organic liquid in which the active material is insoluble or nearly insoluble: certain organic solid materials or inorganic salts can be dissolved in the vehicle to aid in preventing sedimentation or as antigels for water.

A suspension concentrate composition is given here as an example:

SC EXAMPLE 1

| | |
|---|---|
| active material | 500 g |
| polyethoxylated tristyrylphenyl phosphate | 50 g |
| polyethoxylated alkylphenol | 50 g |
| sodium polycarboxylate | 20 g |
| ethylene glycol | 50 g |
| organopolysiloxane oil (antifoaming agent) | 1 g |
| polysaccharide | 1.5 g |
| water | 316.5 g |

Wettable powders (or powder to be sprayed) are generally prepared so that they contain 20 to 95% of active material, and they generally contain, in addition to the solid vehicle, from 0 to 30% of a wetting agent, from 3 to 20% of a dispersing agent and, when this is necessary, from 0.1 to 10% of one or more stabilizing agents and/or other additives, such as penetrating agents, adhesives, or anticlumping agents, dyes, and the like.

To obtain powders to be sprayed or wettable powders, the active materials are intimately mixed, in suitable mixers, with the additional substances and the mixture is milled with mills or other suitable grinders. Powders to be sprayed are thereby obtained with advantageous wettability and suspensibility; they can be suspended in water at any desired concentration and these suspensions can be used very advantageously in particular for application to plant leaves.

Pastes can be produced in place of wettable powders. The conditions and modes of production and use of these pastes are similar to those of wettable powders or powders to be sprayed.

Various wettable powder (or powder to be sprayed) compositions are given here as examples:

| | |
|---|---|
| WP Example 1 | |
| active material | 50% |

-continued

| | |
|---|---|
| ethoxylated fatty alcohol (wetting agent) | 2.5% |
| ethoxylated phenylethylphenol (dispersing agent) | 5% |
| chalk (inert vehicle) | 42.5% |
| WP Example 2: | |
| active material | 10% |
| C13 branched-type synthetic oxo alcohol, ethoxylated with 8 to 10 molecules of ethylene oxide (wetting agent) | 0.75% |
| neutral calcium lignosulphonate (dispersing agent) | 12% |
| calcium carbonate (inert filler) | qs for 100% |
| WP Example 3: | |
| This wettable powder contains the same ingredients as in the above example, in the proportions below: | |
| active material | 75% |
| wetting agent | 1.50% |
| dispersing agent | 8% |
| calcium carbonate (inert filler) | qs for 100% |
| WP Example 4: | |
| active material | 90% |
| ethoxylated fatty alcohol (wetting agent) | 4% |
| ethoxylated phenylethylphenol (dispersing agent) | 6% |
| WP Example 5: | |
| active material | 50% |
| mixture of anionic and nonionic surface-active agents (wetting agent) | 2.5% |
| sodium lignosulphonate (dispersing agent) | 5% |
| kaolin clay (inert vehicle) | 42.5% |

Aqueous dispersions and emulsions, for example the compositions obtained by diluting a wettable powder or an emulsifiable concentrate according to the invention with water, are contained within the general scope of the present invention. Emulsions can be of the water-in-oil or oil-in-water type and they can have a thick consistency, like that of a “mayonnaise”.

The fungicidal compositions according to the invention can be formulated in the form of water-dispersible granules, which also come within the scope of the invention.

These dispersible granules, with a bulk density generally of between approximately 0.3 and 0.6, have a particle size generally of between approximately 150 and 2000 and preferably between 300 and 1500 microns.

The active material content of these granules is generally between approximately 1% and 90%, and preferably between 25% and 90%.

The rest of the granule comprises a solid filler and, optionally, of surface-active adjuvants which confer water-dispersibility properties on the granule. These granules can be essentially of two distinct types according to whether the filler chosen is soluble or insoluble in water. When the filler is water-soluble, it can be inorganic or, preferably, organic. Excellent results were obtained with urea. In the case of an insoluble filler, the latter is preferably inorganic, such as, for example, kaolin or bentonite. It is then advantageously accompanied by surface-active agents (in a proportion of 2 to 20% by weight of the granule) of which more than half comprises, for example, at least one dispersing agent, essentially anionic, such as an alkali metal or alkaline-earth metal polynaphthalenesulphonate or an alkali metal or alkaline-earth metal lignosulphonate, the remainder consisting of nonionic or anionic wetting agents such as an alkali metal or alkaline-earth metal alkylnaphthalenesulphonate.

Moreover, although this is not indispensable, it is possible to add other adjuvants such as antifoaming agents.

The granule according to the invention can be prepared by mixing the necessary ingredients and then granulating according to several techniques known per se (granulator, fluid bed, sprayer, extrusion, and the like). The preparation generally finishes with a crushing followed by a sieving to the particle size chosen within the limits mentioned above. Granules obtained as above and then impregnated with a composition containing the active material can alternatively be used.

It is preferably obtained by extrusion, by carrying out the preparation as indicated in the examples below.

DG EXAMPLE 1

Dispersible Granules

90% by weight of active material and 10% of urea in the form of pearls are mixed in a mixer. The mixture is then milled in a pin mill. A powder is obtained which is moistened with approximately 8% by weight of water. The moist powder is extruded in a perforated-roller extruder. A granular material is obtained which is dried, and then crushed and sieved, so as to respectively keep only the granules with a size of between 150 and 2000 microns.

DG EXAMPLE 2

Dispersible Granules

The following constituents are mixed in a mixer:

| | |
|---|---|
| active material | 75% |
| wetting agent (sodium alkylnaphthalene-sulphonate | 2% |
| dispersing agent (sodium polynaphthalene-sulphonate) | 8% |
| water-insoluble inert filler (kaolin) | 15% |

This mixture is granulated on a fluid bed in the presence of water and then dried, crushed and sieved so as to obtain granules with a size of between 0.15 and 0.80 mm.

These granules can be used alone or in solution or dispersion in water so as to obtain the required dose.

As regards the compositions which are suitable for storage and transportation, they more advantageously contain from 0.5 to 95% (by weight) of active material.

The invention also relates to a product comprising at least one compound A and at least one compound B as defined above, for controlling phytopathogenic fungi by simultaneous, sequential or separate application.

Another subject of the invention is a process for controlling the phytopathogenic fungi in a medium, characterized in that at least one compound A and at least one compound B, these compounds being as defined above, and the combination of these compounds being in an effective and non-phytotoxic total quantity, are applied to the said medium.

More precisely, the subject of the invention is a process for the curative or preventive control of fungi which are phytopathogenic, for example, towards crops or lawns, characterized in that an effective and non-phytotoxic amount of a combination of at least one compound A and at least one compound B, for example in a fungicidal composition according to the invention, is generally applied on the aerial parts of plants.

The fungi which are phytopathogenic towards crops which can be combated by this process are in particular those:

from the Oomycetes group:
- from the Phytophthora genus, such as *Phytophthora infestans* (downy mildew of the Solanaceae, in particular of potatoes or tomatoes), *Phytophthora citrophthora, Phytophthora capsici, Phytophthora cactorum, Phytophthora palmivora, Phytophthora cinnamoni, Phytophthora megasperma* or *Phytophthora parasitica,*
- from the Peronosporaceae family, in particular *Plasmopara viticola* (grape downy mildew), *Plasmopara halstedei* (sunflower downy mildew), Pseudoperonospora sp (in particular downy mildew of cucurbits and of hops), *Bremia lactucae* (lettuce downy mildew) or *Peronospora tabacinae* (tobacco downy mildew), from the Adelomycetes group:
- from the Alternaria genus, for example *Alternaria solani* (alternaria disease of the Solanaceae and in particular of tomatoes and potatoes),
- from the Guignardia genus, in particular *Guignardia bidwellii* (black rot of grapes),
- from the Oidiums group, for example grape powdery mildew (*Uncinula necator*); powdery mildew of legumes, for example *Erysiphe polygoni* (powdery mildew of crucifers); *Leveillula taurica, Erysiphe cichoracearum, Sphaerotheca fuligena*; (powdery mildew of cucurbits, of composites or of tomatoes); *Erysiphe communis* (beet and cabbage powdery mildew); *Erysiphe pisi* (pea or lucerne powdery mildew); *Erysiphe polyphaga* (bean and cucumber powdery mildew); *Erysiphe umbelliferarum* (powdery mildew of the Umbelliferae, in particular of carrots); *Sphaerotheca humuli* (hop powdery mildew); or *Erysiphe graminis* (powdery mildew of cereals),
- from the Septoria genus, for example *Septoria nodorum* or *Septoria tritici* (septoria disease of cereals);

from the Sclerotinia genus, for example *Sclerotinia sclerotinium* or *Sclerotinia homeocarpa* (lawn sclerotinia disease), from the Basidiomycetes group:
- from the Puccinia genus, for example *Puccinia recondita* or *striiformis* (wheat rusts),
- of the Rhizoctonia spp. family.

A classification made no longer by targeted fungi but by target crops can be illustrated as below:

barley-helminthosporium (Helminthosporium), rape: alternaria (Alternaria spp.), rot (*Botrytis cinerea*), sclerotinia disease (*Sclerotinia sclerotinium*)

grapes: powdery mildew (*Uncinula necator*), downy mildew (*Plasmopara viticola*), rot (*Botrytis cinerea*), excoriosis (*Phomopsis viticola*) and black rot (*Guignardia bidwellii*), Solanaceae: downy mildew (*Phytophthora infestans*), alternaria disease (*Alternaria solani*) and rot (*Botrytis cinerea*), legumes: downy mildews (Peronospora spp., *Bremia lactucae*, Pseudoperonospora spp.), or alternaria disease (Alternaria spp.), sclerotinia disease (Sclerotinia spp.), rot (*Botrytis cinerea*) or powdery mildew (Erysiphe spp. or *Sphaerotheca fuliginea*), foot or root rot (Rhizoctonia spp.), rice: foot or root rot (Rhizoctonia spp.), arboriculture: scab (*Venturia inaegualis*), powdery mildew (*Podosphaera leucotricha*), alternaria disease (Alternaria spp.), rot (*Botrytis cinerea*) and monilia disease (*Monilia fructigena*), citrus fruits: scab (*Elsinoe fawcetti*), melanose (*Phomopsis citri*) and diseases due to Phytophthora spp., bananas: cercospora disease (*Mycosphaerella figiensis*), lawns: rust, powdery mildew, helminthosporium disease or soil diseases (*Microdochium nivale*, Pythium spp., *Rhizoctonia solani, Sclerotinia homeocarpa* and the like).

The fungicidal composition which is the subject of the invention is applied by means of various treatment processes, such as:

spraying a liquid comprising the said composition on the aerial parts of the crops to be treated, dusting, the incorporation of granules or of powders into the soil, sprinkling, injecting into trees or painting.

The spraying of a liquid on the aerial parts of the crops to be treated is the preferred treatment process.

"Effective and non-phytotoxic amount" is understood to mean an amount of composition according to the invention which is sufficient to make possible control or destruction of the fungi present or capable of appearing on the crops and which does not result in any notable phytotoxicity symptoms with respect to the said crops. Such an amount is capable of varying within wide limits depending on the fungi to be combated, the type of crop, the weather conditions and the compounds included in the fungicidal composition according to the invention. This amount can be determined by systematic tests in the field, within the scope of the person skilled in the art.

The use doses during the implementation of the process according to the invention will then generally be:

on barley, rape, rice, grapes, legumes, Solanaceae, bananas, arboriculture or citrus fruits:

100 to 1000 g of compound B, e.g. iprodione+50 to 500 g/ha of compound A and more precisely 300 to 600 g+100 to 400 g/ha, i.e. a total dose of compounds A and B of between 150 and 1500 g/ha, preferably between 400 and 1000 g/ha, on lawns:

1000 to 5000 g of compound B, e.g. iprodione+100 to 2000 g/ha of compound A and more precisely 2000 to 4000 g+250 to 1000 g/ha, i.e. a total dose of compounds A and B of between 1100 and 7000 g/ha, preferably between 2250 and 5000 g/ha.

The following examples are given purely by way of illustration of the invention, which they do not limit in any way.

In the figure appended to the present text, the dose of each active material, taken in isolation, required for control of the phytopathogenic fungus at the level indicated is compared with that of the 2 active materials taken as a mixture. The effective dose of each active material taken in isolation is shown on the axis of the abscissae and of the ordinates and a straight line is traced cutting these 2 axes and connecting these 2 doses. When an active material taken in isolation is not effective, the straight line is parallel to the axis of the coordinates which shows the doses of this active material. As regards the 2 active materials taken as a mixture, the dose of the mixture at a given ratio is shown by a point.

EXAMPLE 1

In Vivo Test of the Combination of ICIA5504 with Iprodione with Respect to Alternaria Disease of Radish (*Alternaria brassicae*) by Preventive Treatment 24 Hours Before Infection A suspension comprising the compounds A and B in a liquid mixture composed of a surface-active agent (oleate of polyoxyethylenated derivative of sorbitan) and water is prepared.

The component B is iprodione; the A/B ratio is 0.25, 0.5, 1, 2 or 4.

Radish seedlings (variety Pernot), are grown in small pots. When these seedlings are 10–12 days old (cotyledon, 1st leaf stage), they are treated by spraying with the above suspension.

Seedlings, used as controls, are treated with a similar suspension but which does not contain active material ("formulation blank").

After 24 hours, each seedling is infected by spraying with an aqueous suspension of spores of *Alternaria brassica*, which suspension is obtained from an in vitro culture of the fungus. These spores are suspended at a concentration of 40,000 units per $cm^3$ of inoculum. Infection is carried out by spraying the inoculum at the top surface of the leaves.

The infected seedlings are then incubated for six days at 18–20° C. at 90–100% relative humidity under natural light.

Reading is carried out 6 days after infection, in comparison with the control seedlings.

The results obtained are reported in the form of points, corresponding to 80% destruction of the parasite, and are plotted on a Tammes isobole diagram which contains, on the abscissa, the doses of A expressed in ppm (mg/l) and, on the ordinate, the doses of B, also in ppm (mg/l).

The diagram of FIG. 1 is obtained. It appears that the addition of iprodione makes it possible, in an entirely unexpected way, to lower the dose of A necessary for the destruction of 80% of the parasite below 115 ppm (mg/l), which corresponds to the dose of A alone which it is necessary to apply to obtain the same percentage of destruction.

The arrangement of the points obtained therefore shows a bilateral effect described, according to the Tammes method mentioned above, as a "two-sided effect". This arrangement corresponds to a type-III isobole according to the said method (page 74 of the corresponding bibliographical reference already cited) and is characteristic of a synergy.

EXAMPLE 2

In Vivo Test of the Combination of ICIA5504 with Iprodione with Respect to Helminthosporium Disease of Barley by Preventive Treatment 7 Days Before Infection The fungicides are used at the following doses:

| |
|---|
| iprodione (Rovral SC 500 g/l (B): 12.5-25-50-100-200-400-800 g/ha, |
| ICZ A5504 (SC 250 g/l) (A): 1.5-3.1-6.2-12.5-25-50-100-200 g/ha, |
| iprodione (B)/ICIA5504(A) = 4: 6.2 + 1.5 to 800 + 200 g/ha, |
| iprodione/ICIA5504 = 2: 3.1 + 1.5 to 400 + 200 g/ha |
| iprodione/ICIA5504 = 1: 1.5 + 1.5 to 200 + 200 g/ha |
| iprodione/ICIA5504 = 0.5: 0.75 + 1.5 to 100 + 200 g/ha |

The young barley plants (var. Express) which are 12 days old (first leaf developed stage) are treated with the experimental fungicides at the doses indicated above in a slurry volume of 250 l/ha (3 repeats/dose). Seven days after the treatment, the young barley plants are infected with a suspension of *Pyrenophora teres* spores (10,000 spores/ml). The young plants are incubated for 48 hours at 20° C., 100% relative humidity (RH). Next, the plants are transferred to a greenhouse at 20° C., 70–80% RE under natural light. The grading of the disease is carried out ten days after infection by estimating the leaf surface area contaminated on the first leaf (10 young plants/pot).

By comparing with the control (non-treated-contaminated) a percentage efficacy is calculated. The synergy is then quantified by using the Colby model. The following results are thereby obtained:

| B/A | 0 g/ha | 1.5 | 3.1 | 6.2 | 12.5 | 25 | 50 | 100 | 200 |
|---|---|---|---|---|---|---|---|---|---|
| | | | | Observed efficacy | | | | | |
| 0 g/ha | 0 | 0 | 17.54 | 34.21 | 59.21 | 76.75 | 83.86 | 81.67 | 92.72 |
| 12.5 | 15.79 | | 78.6 | 88.68 | 83.95 | 94.04 | | | |
| 25 | 7.02 | | | 88.77 | 94.47 | 85.70 | 93.68 | | |
| 50 | 37.72 | | | | 91.49 | 96.23 | 92.54 | 90.88 | |
| 100 | 35.09 | | | | | 94.65 | 95.53 | 93.33 | 96.23 |
| 200 | 47.37 | | | | | | 95.53 | 97.37 | 95 |
| 400 | 50.88 | | | | | | | 96.14 | 97.72 |
| 800 | 59.65 | | | | | | | | 95.95 |
| | | | | Theoretical efficacy according to Colby | | | | | |
| 0 g/ha | 0 | 0 | 17.54 | 34.21 | 59.21 | 76.75 | 83.86 | 81.67 | 92.72 |
| 12.5 | 15.79 | | 30.56 | 44.60 | 65.65 | 80.42 | | | |
| 25 | 7.02 | | | 38.83 | 62.07 | 78.38 | 84.99 | | |
| 50 | 37.72 | | | | 74.60 | 85.52 | 89.95 | 88.58 | |
| 100 | 35.09 | | | | | 84.91 | 89.52 | 88.10 | 95.27 |
| 200 | 47.37 | | | | | | 91.51 | 90.35 | 96.17 |
| 400 | 50.88 | | | | | | | 91.00 | 96.42 |
| 800 | 59.65 | | | | | | | | 97.06 |
| | | | | Synergy (% gain) | | | | | |
| 0 g/ha | | | | | | | | | |
| 12.5 | | | +48 | +44 | +18 | +14 | | | |
| 25 | | | | +50 | +32 | +7 | +9 | | |
| 50 | | | | | +17 | +11 | +3 | +2 | |
| 100 | | | | | | +10 | +6 | +5 | +1 |
| 200 | | | | | | | +4 | +7 | −1 |
| 400 | | | | | | | | +5 | +1 |
| 800 | | | | | | | | | −1 |

What is claimed is:

1. A fungicidal composition comprising a synergistic fungicidally effective amount of a compound A which is methyl (E)-2-{2-[6-(2-cyanophenoxy)pyrimidin-4 -yloxy] phenyl}-3-methoxyacrylate and a compound B which is iprodione, the A/B ratio by weight being between 0.02 and 5.

2. A fungicidal composition according to claim 1, wherein the A/B ratio by weight is between 0.0625 and 1.33.

3. A fungicidal composition according to claim 1, wherein the A/B ratio by weight is between 0.05 and 5.

4. A fungicidal composition according to claim 1, wherein the A/B ratio by weight is between 0.17 and 1.33.

5. A fungicidal composition according to claim 1, wherein the A/B ratio by weight is between 0.02 and 2.

6. A fungicidal composition according to claim 1, wherein the A/B ratio by weight is between 0.0625 and 0.25.

7. A fungicidal composition according to claim 1, wherein the A/B ratio by weight is between 0.25 and 4.

8. A fungicidal composition according to claim 1, further comprising at least one member selected from the group consisting of an agriculturally acceptable solid or liquid vehicle and an agriculturally acceptable surface-active agent.

9. A fungicidal composition according to claim 8, comprising from 0.05% to 95% by weight of compounds A and B.

10. A process for the curative or preventative control of phytopathogenic fungi in plants, said process comprising applying to plants or to the locus in which they grow a synergistic fungicidally effective non-phytotoxic amount of a compound A which is methyl (E)-2-{2-[6-(2-cyanophenoxy)pyrimidin-4-yloxy]phenyl}-3-methoxyacrylate and a compound B which is iprodione, the A/B ratio by weight being between 0.02 and 5.

11. A process according to claim 10, wherein the A/B ratio by weight is between 0.0625 and 1.33.

12. A process according to claim 10, wherein the A/B ratio by weight is between 0.25 and 4.

13. A process according to claim 10, wherein the synergistic fungicidally effective non-phytotoxic amount of A and B is applied to crops or lawns to control fungi which are phytopathogenic towards crops or lawns, respectively.

14. A process according to claim 13, wherein the synergistic fungicidally effective non-phytotoxic amount of A and B is applied to the aerial parts of the plants.

15. A process according to claim 13, wherein the synergistic fungicidally effective non-phytotoxic amount of A and B is applied to crops and wherein the A/B ratio by weight is between 0.05 and 5.

16. A process according to claim 13, wherein the synergistic fungicidally effective non-phytotoxic amount of A and B is applied to crops and wherein the A/B ratio by weight is between 0.17 and 1.33.

17. A process according to claim 13, wherein the synergistic fungicidally effective non-phytotoxic amount of A and B is applied to crops at a dose rate of between 150 and 1500 g/ha.

18. A process according to claim 13, wherein the synergistic fungicidally effective non-phytotoxic amount of A and B is applied to crops at a dose rate of between 400 and 1000 g/ha.

19. A process according to claim 13, wherein the synergistic fungicidally effective non-phytotoxic amount of A and B is applied to lawns and wherein the A/B ratio by weight is between 0.02 and 2.

20. A process according to claim 13, wherein the synergistic fungicidally effective non-phytotoxic amount of A and B is applied to lawns and wherein the A/B ratio by weight is between 0.0625 and 0.25.

21. A process according to claim 13, wherein the synergistic fungicidally effective non-phytotoxic amount of A and B is applied to lawns at a dose rate of between 1100 and 7000 g/ha.

22. A process according to claim 13, wherein the synergistic fungicidally effective non-phytotoxic amount of A and B is applied to lawns at a dose rate of between 2250 and 5000 g/ha.

* * * * *